United States Patent [19]

Hubis

[11] Patent Number: 4,478,665
[45] Date of Patent: Oct. 23, 1984

[54] METHOD FOR MANUFACTURING HIGHLY POROUS, HIGH STRENGTH PTFE ARTICLES

[75] Inventor: Daniel E. Hubis, Elkton, Md.

[73] Assignee: W. L. Gore & Associates, Inc., Newark, Del.

[21] Appl. No.: 459,804

[22] Filed: Jan. 21, 1983

Related U.S. Application Data

[62] Division of Ser. No. 204,509, Nov. 6, 1980, Pat. No. 4,385,093.

[51] Int. Cl.$^3$ .................. B29C 17/02; B29D 27/00
[52] U.S. Cl. ............................. 156/229; 264/127; 264/288.8
[58] Field of Search .................. 264/127, 288.8; 156/228, 229

[56] References Cited

U.S. PATENT DOCUMENTS

| | | |
|---|---|---|
| 612,897 | 10/1898 | Ellio . |
| 2,964,065 | 12/1960 | Haroldson et al. ............... 264/175 |
| 3,207,644 | 9/1965 | Hobson et al. . |
| 3,767,500 | 10/1973 | Tally et al. . |
| 3,887,761 | 6/1975 | Gore . |
| 3,953,566 | 4/1976 | Gore . |
| 3,962,153 | 6/1976 | Gore ................................ 264/127 |
| 4,061,517 | 12/1977 | Dulton et al. . |
| 4,187,390 | 2/1980 | Gore . |
| 4,283,448 | 8/1981 | Bowman .......................... 264/248 |

FOREIGN PATENT DOCUMENTS

| | | | |
|---|---|---|---|
| 2409178 | 8/1974 | Fed. Rep. of Germany ...... 264/127 |
| 54-97686 | 8/1979 | Japan ................................ 156/229 |
| 6511556 | 3/1966 | Netherlands ..................... 264/127 |

*Primary Examiner*—James Lowe
*Attorney, Agent, or Firm*—John S. Campbell

[57] ABSTRACT

A method for producing a multi-component, porous PTFE article. Components of PTFE containing a liquid lubricant are placed in intimate contact, dried and then stretched in one or more directions. The PTFE components may optionally contain a filler. The resultant product has a virtually uninterrupted structure at the join and possesses very high bond strengths.

29 Claims, 4 Drawing Figures

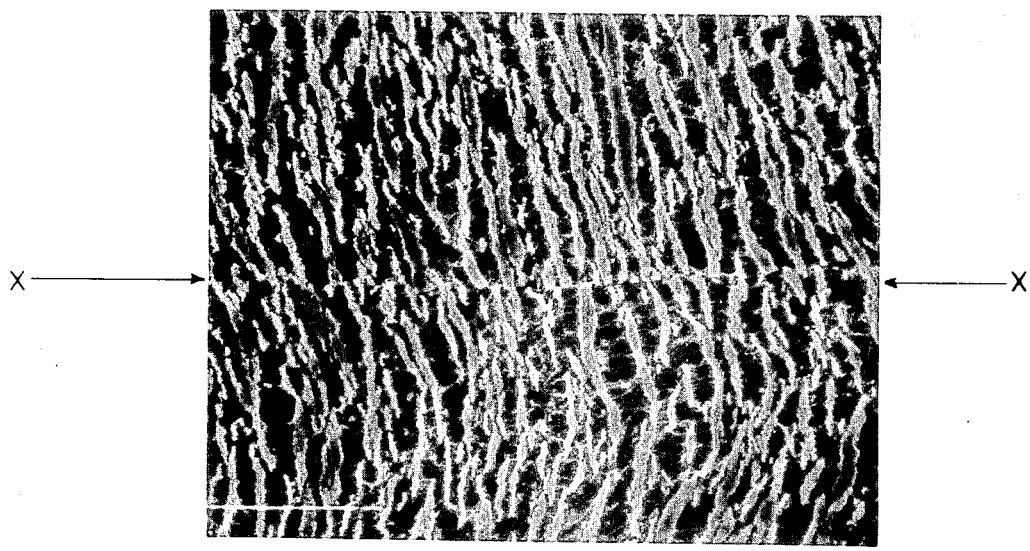
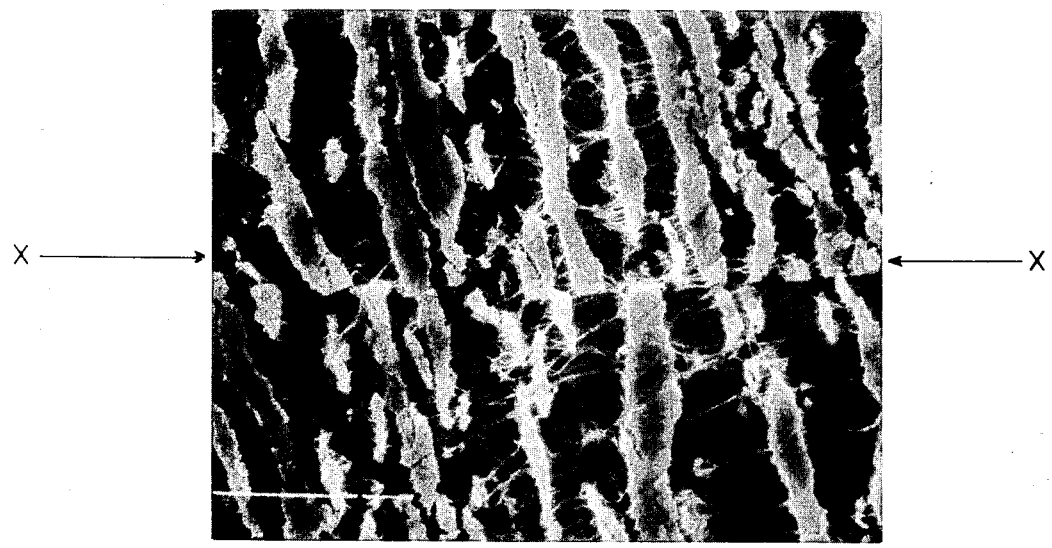
FIG. 4

METHOD FOR MANUFACTURING HIGHLY POROUS, HIGH STRENGTH PTFE ARTICLES

REFERENCE TO RELATED APPLICATIONS

This application is a divisional of United States patent application Ser. No. 204,509, filed Nov. 6, 1980 now U.S. Pat. No. 4,385,093.

FIELD OF THE INVENTION

This invention relates to a process for producing highly porous, high strength, multi-component articles of polytetrafluoroethylene. These products possess high inter-component strength and exhibit substantially no change in porosity at the interface between the components.

BACKGROUND OF THE INVENTION

Polytetrafluoroethylene (hereinafter "PTFE") has excellent heat resistance, chemical resistance, insulative properties, non-adhesiveness and self-lubrication. This polymer has found wide use in medical, industrial and recreational fields.

U.S. Pat. No. 3,953,566 provides a method for producing a wide variety of shaped articles such as films, tubes, rods and continuous filaments. The articles so produced are characterized by a unique combination of high strength and high porosity. The articles, themselves, are covered by U.S. Pat. No. 4,187,390. The microstructure of these articles consists of nodes interconnected by fibrils.

Subsequent work lead to the discovery that expanded PTFE tubes, made according to the teachings of U.S. Pat. No. 3,953,566 in which the distance between nodes ranged from 5–1,000 microns was especially useful as a vascular prosthesis. On implantation in the human body this microstructure is readily invaded by body tissue.

It was also discovered that products could be produced by very high elongation processes, in excess of 50:1. Such products are covered by U.S. Pat. No. 3,962,153. However, studies of the product made by U.S. Pat. No. 3,962,153 at extremely high stretch amounts show that the number of visible nodes were considerably less than the number per unit sample size obtained at lower stretch amounts. The microstructure of these highly stretched samples appeared to be, principally, highly oriented fibrils, oriented parallel to the stretching direction, separated by void spaces, and containing very small and relatively few nodes.

It is thought that the nodes have been largely drawn into fibrils. Although these products are extremely valuable for many applications such as high strength packing fibers and sewing thread, the reduction of the node structure is undesirable for other end uses. The strength of these products is predominately in the direction of orientation; the strength in the other directions being comparatively weak.

In certain areas it was desirable to have thicker material that was routinely produced by the process of U.S. Pat. No. 3,953,566. A first approach to achieving this would be to start the expansion process with a thicker extrudate. When one considers all the variables involved in paste extrusion, however, it was realized that the extrusion of extrudates with cross-sectional areas greater than about 2 square inches would involve practical extruder designs.

The next step involved the assembly of a multiplicity of thin components to give a thicker component.

A number of prior art methods have been utilized to bond multiple layers of porous PTFE together including:

(1) placing layers of porous PTFE in contact and under pressure and heating above the crystalline melt point of PTFE;
(2) bonding layers of porous PTFE using bonding agents such as silicone adhesives or FEP, a copolymer of tetrafluoropropylene and hexafluoropropylene;
(3) mechanically connecting porous layers using various sewing and/or weaving techniques.

The above described methods suffer from one of more of the following disadvantages:

(a) inadequate interlayer bonding;
(b) altered porosity either at the layer interface or within the bulk of the layer;
(c) the presence of contaminating material.

Specifically in the area of filtration, the microstructure of nodes and fibrils present in products produced by the process of U.S. Pat. No. 3,953,566, and defined in U.S. Pat. No. 4,187,390 is particularly desirable. Interruption of this microstructure of the bond severely affects the utility of the product.

BRIEF DESCRIPTION OF THE INVENTION

This invention provides a process whereby composite articles of expanded PTFE of any desired thickness and porosity may be produced. The resultant article has a virtually unchanged porosity at the interface and possess very high inter-component bond strength. The product of this invention is produced by placing in intimate contact a plurality of highly crystalline PTFE components while they contain lubricant. The components can then be further processed in a variety of ways as described herein.

BRIEF DESCRIPTION OF DRAWINGS

FIG. 3 and FIG. 4 are scanning electronmicrographs at 300X and 900X of two layers which have been bonded together by simply placing expanded layers in contact and heating above the crystalline melt point. Again X—X indicates the join.

DETAILED DESCRIPTION OF THE INVENTION

Figure 1:
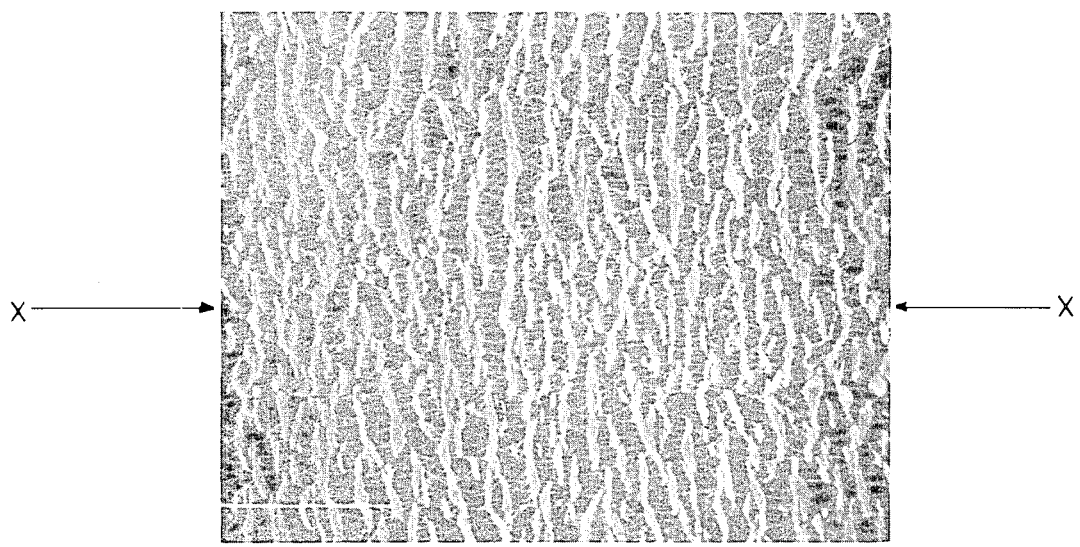
FIG. 1 and FIG. 2 are scanning electronmicrographs of a product of the present invention at 300X and 900X respectively. The arrows X—X indicate the join.

The key to this invention is the placing of PTFE components containing lubricant, in intimate contact, at a step in the processing operation. Such components are termed "wet" components.

The preferable step in the process to place the components in contact is at the beginning. At the beginning, is intended to indicate that the PTFE components be placed in contact in extrudate form while still containing extrusion aid. This ensures that the maximum amount of PTFE is in contact with PTFE, thereby promoting the formation of a node-fibril structure across the interface on subsequent processing. As a result, very high inter-component bond strengths are achieved. The bond strengths achieved by this invention equal or exceed the Z direction strength of the individual components. The Z direction strength and/or bond strength is measured by punching out at 1.5 cm diameter disc of the sample to be tested. This disc is epoxy glued between two metal cylinders attached to which are high tenacity PTFE fibers. The ends of the fibers are clamped between Instron jaws and the sample pulled at a rate of 10" per minute.

This invention further allows the production of high strength, highly porous, multi-component PTFE articles that contain up to 50% by weight of filler. Suitable fillers can be obtained from a wide group such as carbon black, graphite, pigments, titanium dioxide, zirconium dioxide, asbestos, silica, mica, potassium titanate, and dielectric fluids such as polysiloxane. The invention can also be used to bond combinations of filled and non-filled components together.

The intimacy of contact between components can be enhanced by applying a compressive force for contact. This can be achieved by a variety of techniques such as a press or a set of calender rolls depending on the configuration of the components.

Although the description of the invention and processing will largely relate to the preferred embodiment, that is, placing multiple components of wet extrudate in contact, the invention is not so limited. PTFE components which have been expanded and are porous can be wetted with lubricant, placed in contact, dried and further expanded. Since these components are more porous than extrudate, there is less chance of PTFE being in contact with PTFE and consequently less strength is developed between the layers.

After the PTFE wet extrudates have been placed in contact for a sufficient period of time, which must be determined experimentally if no compressive force such as calendering is used, they can be processed in a variety of ways:

1. The wet multi-component extrudate can be dried, that is, the lubricant can be removed, and the dried multi-component extrudate can be expanded according to the teachings of U.S. Pat. No. 3,953,566.

2. The wet multi-component extrudate can be stretched with the lubricant present. A final product can be obtained by removal of the lubricant or after removal of the lubricant further processings can be done according to the teachings of U.S. Pat. No. 3,953,566.

The final product can optionally, in either case, be used as is, partially sintered or fully sintered. Sintering is heating the PTFE to a temperature above the crystalline melt point of the virgin polymer for a sufficient time such that on cooling a new form and degree of crystalline PTFE is formed. The amount of sintering can be determined by thermal analysis.

Moreover, a further stretching operation can be performed above the crystalline melt point if desired.

Multi-component filled materials containing hydrophilic agents such as $TiO_2$ are useful in electrochemical cells such as those used to make chlorine and caustic soda. The high intercomponent bond strength is necessary to prevent the components being separated by gases generated within the components.

The multi-component material can contain gas absorbing agents such as activated charcoal.

The invention will further be described by the following examples which serve to illustrate, but not limit the invention.

EXAMPLE I

A mixture of 16 parts by weight of titanium dioxide available from DeGussa, Inc. under the trade designation "Titanium Dioxide #P-25" and having a mean particle diameter of about 20 nanometers was co-coagulated with 84 parts by weight of PTFE in a 30% solids non-stabilized dispersion. After drying to remove the liquids, the compound was lubricated at 200 cc of extrusion aid (available under the trade designation "ISOPAR K" from Exxon) per pound of powder. The mixture was then extruded into a sheet 0.090" thick and 6" wide. Four equal lengths of this 0.090" extrudate were stacked one on top of another and calendered from a total thickness of 0.360" to 0.210". The liquid was removed by heating the composite to a temperature above the boiling point of the lubricant.

To determine the Z direction strength, a single 0.090" extrudate was calendered to 0.070" and then dried.

A 2" sample of both the multi-component and the single component were then expanded to 10" at a rate of 750% per second.

A second and third 2" sample of the single component were also expanded to 10" at a rate of 750% per second.

The multi-layer expanded sample was immersed in a molten salt solution at 365° C. for 2 minutes.

A single layer expanded sample was immersed in a molten salt solution at 365° C. for one minute. Two of the single layer expanded samples were placed in contact, held restrained and placed in a molten salt solution at 365° C. for 2 minutes.

Figure 2:
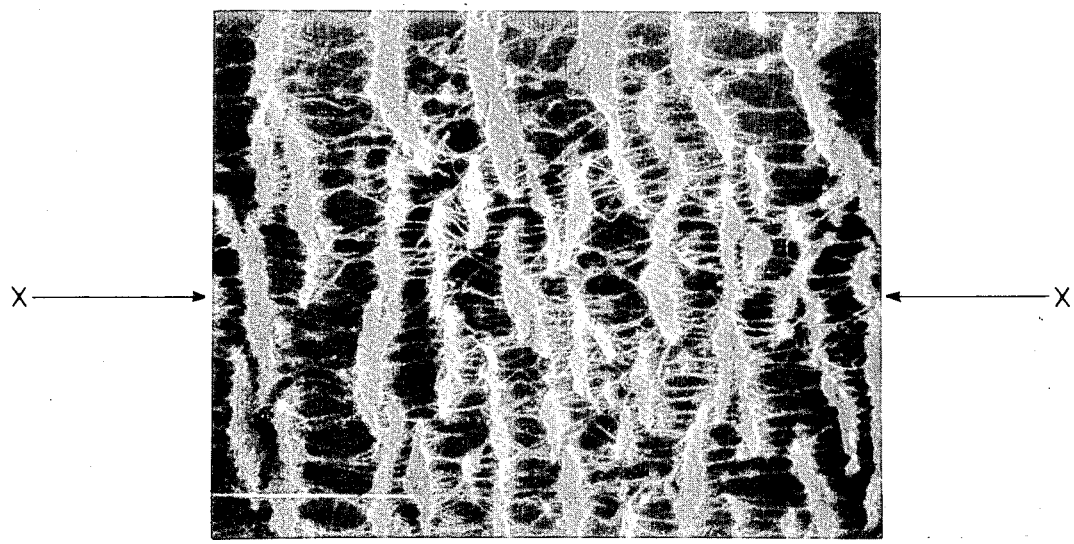

Z direction strength measurements were made of the following samples:

1. Single component extrudate.
2. Multi-component extrudate.
3. Single component expanded sample.
4. Multi-component expanded sample.
5. Single component expanded, sintered.
6. Multi-component expanded, sintered (FIG. 1 & FIG. 2).
7. 2-layers bonded by sintering (FIG. 3 & FIG. 4).

The Z direction strength is given in Table I.

TABLE I

| RESULTS | CALENDERED SINGLE-COMPONENT | CALENDERED MULTI-COMPONENT | TWO LAYER |
| --- | --- | --- | --- |
| Extrudate | 34.0 psi | 31.0 psi | — |
| Expanded | 6.0 psi | 7.3 psi | — |
| Extrudate Expanded, 365° C. | 162.0 psi | 190.0 psi | 15 psi |

EXAMPLE II

A mixture of titanium dioxide and PTFE co-coagulated and dried as in Example I. The mixture was chilled to 0° C., screened, lubricated with 155 cc of ISOPAR K extrusion aid per pound of powder. The mixture was preformed and extruded into a sheet 0.090" thick by 6" wide. This extrudate was then calendered to 0.085" thick. Four layers of this extrudate were placed one on top of another and calendered from a total thickness of 0.340" to 0.195".

The multi-component sheet, still containing lubricant, was then pulled transversely from 4–5" to 13" in a longitudinal distance of 32" on a tenter frame with a longitudinal speed of 6 feet per minute.

The multi-component sample was then restrained and dried from 2–5 hours at 190° C. After the lubricant had been removed by the drying step, the sample was heated to 100° C. and again pulled transversely from 8.5" to 23" on the same tenter frame at the same speed.

Attempts to separate components by hand and observation indicated that the individual components could not be separated.

EXAMPLE III 50 parts by weight of "YF Nut Shell Charcoal Powder" available from Barnebey Cheney were co-coagulated with 50 parts by weight of PTFE in a 30% solids non-stabilized dispersion.

After drying, the compound was chilled to 0° C., screened and lubricated with 200 cc of ISOPAR K solvent per pound of compound. The mixture was preformed and extruded into a 0.100" diameter bead. This bead was calendered to 0.030" thickness and placed on top of a previously calendered 0.008" thick sheet, both still containing lubricant. The two-component samples were calendered to 0.020", then dried at 200° C. The sample was then heated to 250° C. and hand stretched approximately 2:1. The stretched sample was then immersed in a molten salt bath at 365° C. for 45 seconds.

Upon observation and physical testing, failure occurred not at the interface, but within the filled component.

EXAMPLE IV 16 parts by weight of titanium dioxide, available under the trade designation "P-25" form DeGussa, Inc., was co-coagulated with 84 parts by weight of PTFE in a 30% solids non-stabilized dispersion.

After drying, the compound was lubricated with 155 cc of ISOPAR K solvent, preformed and extruded into a 0.090" thick, 6" wide sheet and calendered to 0.085". Four layers of the 0.085" sheet were placed on top of one another and calendered together to reduce the thickness from 0.340" to 0.195". The multi-component sample was then dried to remove the lubricant.

A 4"×4" section of this multi-component sample was placed in a pantograph and heated to 250° C. for 6 minutes, then pulled simultaneously, longitudinally and transversely to 12.7"×12.7" at an axis pull speed of 16.7" per second.

This sample was then placed in a molten salt bath at 365° C. for one minute.

Upon physical testing and observation, the individual components could not be separated at the interface.

I claim:

1. A process for making a multi-layer article of porous expanded polytetrafluoroethylene comprising:
   (a) intimately superimposing on top of one another at least two layers of unsintered polytetrafluoroethylene containing a liquid lubricant, at a temperature below the crystalline melt point of polytetrafluoroethylene;
   (b) removing said lubricant from said multi-layer article;
   (c) expanding in at least one direction said multi-layer article, from which the lubricant has been removed, at a rate exceeding 10% per second at an elevated temperature below the crystalline melt point of polytetrafluorethylene.

2. The process of claim 1 wherein said contacting is performed in the nip between two calender rolls.

3. The process of claim 1 wherein said expansion is performed at a rate exceeding 50% per second.

4. The process of claim 1 wherein said expansion is performed at a rate exceeding 1000% per second.

5. The process of claim 1 wherein said expansion is performed at a rate exceeding 10,000% per second.

6. The process of claim 1 wherein said expansion is biaxial.

7. The process of claim 6 wherein said biaxial expansion is performed simultaneously.

8. The process of claim 1 wherein said expansion is multi-axial.

9. The process of claim 8 wherein said multi-axial expansion is performed simultaneously.

10. The process of claim 1 wherein at least one of said layers contains a filler.

11. The process of claim 10 wherein said filler is a pigment.

12. The process of claim 10 wherein said filler is $TiO_2$.

13. The process of claim 12 wherein said filler is $TiO_2$ having an average particle diameter of about 20 nanometers.

14. The process of claim 10 wherein said filler is carbon black.

15. The process of claim 10 wherein said filler is a mica.

16. The process of claim 10 wherein said filler is asbestos.

17. The process of claim 10 wherein said filler is silica.

18. The process of claim 10 wherein said filler is glass.

19. The process of claim 10 wherein said filler is potassium titinate.

20. The process of claim 10 wherein said filler is a dielectric fluid.

21. The process of claim 10 wherein said filler is polysiloxane.

22. The process of claim 1 wherein said multi-layer article after expansion is heated to a temperature above the crystalline melt point of polytetrafluoroethylene to partially sinter said article.

23. The process of claim 1 wherein said multi-layer article after expansion is heated to a temperature above the crystalline melt point of polytetrafluoroethylene to fully sinter said article.

24. The process of claim 22 wherein said article is further stretched after heating above the crystalline melt point of polytetrafluoroethylene.

25. The process of claim 23 wherein said article is further stretched after heating above the crystalline melt point of polytetrafluoroethylene.

26. The process of claim 1 in which said layers are extrudates of polytetrafluoroethylene.

27. The process of claim 1 in which said layers are expanded porous polytetrafluoroethylene layers that have been wetted with liquid lubricant.

28. A process for making a multi-layer article of porous expanded polytetrafluoroethylene comprising:
   (a) initially superimposing on top of one another at least two layers of unsintered polytetrafluoroethylene containing a liquid lubricant, at a temperature below the crystalline melt point of polytetrafluoroethylene;
   (b) stretching said multi-layer article at a temperature below the boiling point of said lubricant;
   (c) removing said lubricant from said stretched article;
   (d) expanding said multi-layer article at a rate exceeding 10% per second.

29. The process of claim 28 wherein at least one of said layers contains a filler.

* * * * *